United States Patent [19]
DiPalma et al.

[11] Patent Number: 5,613,961
[45] Date of Patent: Mar. 25, 1997

[54] THIN, CURVED ABSORBENT ARTICLE HAVING ELASTICIZED EDGES

[75] Inventors: Joseph DiPalma, Neenah; Sowmya S. Anjur, Appleton, both of Wis.

[73] Assignee: Kimberly-Clark Corporation, Neenah, Wis.

[21] Appl. No.: 366,845

[22] Filed: Dec. 30, 1994

[51] Int. Cl.$^6$ ..................... A61F 13/15
[52] U.S. Cl. ............... 604/369; 604/385.2; 604/387
[58] Field of Search .................. 604/369, 387, 604/386, 385.2

[56] References Cited

U.S. PATENT DOCUMENTS

| | | | |
|---|---|---|---|
| Re. 33,351 | 9/1990 | Papajohn | 604/387 |
| 907,784 | 12/1908 | Green . | |
| 1,192,439 | 7/1916 | Luellen . | |
| 1,946,626 | 2/1934 | Jurgensen | 128/290 |
| 2,043,325 | 6/1936 | Jackson, Jr. | 128/284 |
| 2,064,431 | 12/1936 | Jurgensen | 128/290 |
| 2,092,346 | 9/1937 | Arone | 128/284 |
| 2,331,355 | 10/1943 | Strongson | 128/290 |
| 2,566,451 | 9/1951 | Julien | 128/290 |
| 2,683,457 | 7/1954 | Cunningham | 128/290 |
| 2,747,575 | 5/1956 | Mercer | 128/290 |
| 2,973,760 | 3/1961 | Dudley | 128/287 |
| 3,092,109 | 6/1963 | Mosier | 128/289 |
| 3,121,427 | 2/1964 | Mosier | 128/284 |
| 3,183,909 | 5/1965 | Roehr | 128/290 |
| 3,262,451 | 7/1966 | Morse | 128/290 |
| 3,444,859 | 5/1969 | Kalwaites | 128/284 |
| 3,572,342 | 3/1971 | Lindquist et al. | 128/287 |
| 3,575,174 | 4/1971 | Mogor | 128/290 |
| 3,595,235 | 7/1971 | Jespersen | 128/284 |
| 3,687,350 | 8/1972 | Warburton | 229/2.5 |
| 3,769,979 | 11/1973 | Freney | 128/290 |
| 3,805,790 | 4/1974 | Kaczmarzyk et al. | 128/290 R |
| 3,844,288 | 10/1974 | Kiela | 128/287 |
| 3,857,394 | 12/1974 | Alemany | 128/260 |
| 3,865,112 | 2/1975 | Roeder | 128/290 R |
| 3,888,254 | 6/1975 | Hendricks | 128/290 R |
| 3,916,900 | 11/1975 | Breyer et al. | 604/369 |
| 4,029,100 | 6/1977 | Karami | 604/369 |
| 4,031,897 | 6/1977 | Graetz | 128/286 |
| 4,046,147 | 9/1977 | Berg | 128/290 R |
| 4,059,114 | 11/1977 | Richards | 128/287 |
| 4,079,739 | 3/1978 | Whitehead | 128/290 R |
| 4,184,498 | 1/1980 | Franco | 128/290 R |
| 4,259,220 | 3/1981 | Bunnelle et al. | 260/27 |
| 4,324,246 | 4/1982 | Mullane et al. | 128/287 |
| 4,340,058 | 7/1982 | Pierce et al. | 128/287 |
| 4,342,314 | 8/1982 | Radel et al. | 128/287 |
| 4,433,972 | 2/1984 | Malfitano | 604/385 |
| 4,458,468 | 7/1984 | Sivilich | 53/428 |

(List continued on next page.)

FOREIGN PATENT DOCUMENTS

| | | |
|---|---|---|
| 0330206A1 | 8/1989 | European Pat. Off. . |
| 0400694A1 | 12/1990 | European Pat. Off. . |
| 0534488A1 | 3/1993 | European Pat. Off. . |
| 0597273A1 | 5/1994 | European Pat. Off. . |
| 0607985A1 | 7/1994 | European Pat. Off. . |
| WO90/04374 | 5/1990 | WIPO . |
| WO93/01781 | 2/1993 | WIPO . |
| WO93/01782 | 2/1993 | WIPO . |
| WO93/12745 | 7/1993 | WIPO . |
| WO93/19711 | 10/1993 | WIPO . |
| WO94/16658 | 8/1994 | WIPO . |
| WO94/27538 | 12/1994 | WIPO . |

OTHER PUBLICATIONS

Stiffness of Paper (Gurley Type Stiffness Tester) Article T 543 pm–84.

*Primary Examiner*—Michael J. Milano
*Attorney, Agent, or Firm*—Mark L. Davis

[57] ABSTRACT

An absorbent article is provided having a liquid-permeable cover, a liquid-impermeable baffle, an absorbent therebetween, and a resilient member positioned along at least one longitudinal side of the absorbent article. The absorbent article further includes a tensioning means which imparts an arcuate shape to the absorbent article. The tensioning device can be positioned along a portion of the upper most surface of the resilient member.

18 Claims, 1 Drawing Sheet

U.S. PATENT DOCUMENTS

| | | | |
|---|---|---|---|
| 4,463,045 | 7/1984 | Ahr et al. | 428/131 |
| 4,490,147 | 12/1984 | Pierce et al. | 604/378 |
| 4,501,586 | 2/1985 | Holtman | 604/380 |
| 4,526,825 | 7/1985 | Whitehead | 428/74 |
| 4,554,191 | 11/1985 | Korpman | 428/35 |
| 4,559,051 | 12/1985 | Hanson | 604/385 R |
| 4,579,556 | 4/1986 | McFarland | 604/385 A |
| 4,624,666 | 11/1986 | DeRossett et al. | 604/366 |
| 4,631,062 | 12/1986 | Lassen et al. | 604/385 R |
| 4,648,876 | 3/1987 | Becker et al. | 604/370 |
| 4,655,759 | 4/1987 | Romans-Hess et al. | 604/385 R |
| 4,657,538 | 4/1987 | Becker et al. | 604/381 |
| 4,657,539 | 4/1987 | Hasse | 604/385.2 |
| 4,661,102 | 4/1987 | Shikata et al. | 604/385 A |
| 4,673,403 | 6/1987 | Lassen et al. | 604/385 R |
| 4,677,810 | 7/1987 | Spano | 53/428 |
| 4,681,577 | 7/1987 | Stern et al. | 604/378 |
| 4,681,578 | 7/1987 | Anderson et al. | 604/385 R |
| 4,681,793 | 7/1987 | Linman et al. | 428/138 |
| 4,685,914 | 8/1987 | Holtman | 604/368 |
| 4,690,679 | 9/1987 | Mattingly, III et al. | 604/383 |
| 4,692,160 | 9/1987 | Nussbaumer | 606/331 |
| 4,699,823 | 10/1987 | Kellenberger et al. | 428/219 |
| 4,701,177 | 10/1987 | Ellis et al. | 604/385 A |
| 4,710,185 | 12/1987 | Sneyd, Jr. et al. | 604/372 |
| 4,710,186 | 12/1987 | DeRossett et al. | 604/383 |
| 4,728,381 | 3/1988 | Jezuit et al. | 156/245 |
| 4,730,761 | 3/1988 | Spano | 225/2 |
| 4,731,065 | 3/1988 | Yamada | 604/355 |
| 4,740,342 | 4/1988 | Menard et al. | 264/549 |
| 4,752,349 | 6/1988 | Gebel | 156/267 |
| 4,753,644 | 6/1988 | Cottenden et al. | 604/378 |
| 4,755,413 | 7/1988 | Morris | 428/138 |
| 4,758,240 | 7/1988 | Glassman | 604/379 |
| 4,770,657 | 9/1988 | Ellis et al. | 604/385 |
| 4,772,282 | 9/1988 | Oakley | 604/385.1 |
| 4,778,372 | 10/1988 | Mutti et al. | 425/294 |
| 4,781,710 | 11/1988 | Megison et al. | 604/378 |
| 4,781,713 | 11/1988 | Welch et al. | 604/385.1 |
| 4,795,454 | 1/1989 | Dragoo | 604/385.2 |
| 4,795,455 | 1/1989 | Luceri et al. | 604/386 |
| 4,798,603 | 1/1989 | Meyer et al. | 604/378 |
| 4,798,638 | 1/1989 | Marbach | 156/69 |
| 4,804,380 | 2/1989 | Lassen et al. | 604/385.1 |
| 4,808,177 | 2/1989 | DesMarais et al. | 604/385.1 |
| 4,814,123 | 3/1989 | Hautemont | 264/40.6 |
| 4,820,295 | 4/1989 | Chapas et al. | 604/385.1 |
| 4,822,332 | 4/1989 | Kajander | 604/16 |
| 4,828,555 | 5/1989 | Hermansson | 604/379 |
| 4,846,824 | 7/1989 | Lassen et al. | 604/385.1 |
| 4,865,597 | 9/1989 | Mason, Jr. et al. | 604/385.1 |
| 4,872,870 | 10/1989 | Jackson | 604/366 |
| 4,886,513 | 12/1989 | Mason, Jr. et al. | 604/385.1 |
| 4,897,084 | 1/1990 | Ternstrom et al. | 604/385.2 |
| 4,908,026 | 3/1990 | Sukiennik et al. | 604/378 |
| 4,923,950 | 6/1990 | Johnson | 604/392 |
| 4,936,839 | 6/1990 | Molee et al. | 604/378 |
| 4,944,735 | 7/1990 | Mokry | 604/385.2 |
| 4,950,262 | 8/1990 | Takagi | 604/385.1 |
| 4,950,264 | 8/1990 | Osborn, III | 604/385.1 |
| 4,988,344 | 1/1991 | Reising et al. | 604/368 |
| 4,988,345 | 1/1991 | Reising | 604/368 |
| 5,013,309 | 5/1991 | Baigas, Jr. et al. | 604/368 |
| 5,021,051 | 6/1991 | Hiuke | 604/385.2 |
| 5,026,364 | 6/1991 | Robertson | 604/385.1 |
| 5,030,229 | 7/1991 | Yang | 604/385.1 |
| 5,032,121 | 7/1991 | Mokry | 604/385.2 |
| 5,037,409 | 8/1991 | Chen et al. | 604/358 |
| 5,053,029 | 10/1991 | Yang | 604/385.1 |
| 5,064,489 | 11/1991 | Ujimoto et al. | 156/164 |
| 5,074,855 | 12/1991 | Rosenbluth et al. | 604/385.1 |
| 5,074,856 | 12/1991 | Coe et al. | 604/385.1 |
| 5,092,860 | 3/1992 | Pigneul | 604/380 |
| 5,098,422 | 3/1992 | Davis et al. | 604/385.1 |
| 5,104,396 | 4/1992 | Oatley et al. | 604/379 |
| 5,129,893 | 7/1992 | Thoren | 604/385.2 |
| 5,134,007 | 7/1992 | Reising et al. | 428/78 |
| 5,135,521 | 8/1992 | Luceri et al. | 604/383 |
| 5,147,343 | 9/1992 | Kellenberger | 604/368 |
| 5,171,302 | 12/1992 | Buell | 604/385.1 |
| 5,178,139 | 1/1993 | Angelillo et al. | 128/403 |
| 5,181,563 | 1/1993 | Amaral | 604/385.2 |
| 5,197,959 | 3/1993 | Buell | 604/385.1 |
| 5,207,662 | 5/1993 | James | 604/387 |
| 5,211,641 | 5/1993 | Roos et al. | 604/385.1 |
| 5,219,341 | 6/1993 | Serbiak et al. | 604/361 |
| 5,234,422 | 8/1993 | Sneller et al. | 604/385.2 |
| 5,248,309 | 9/1993 | Serbiak et al. | 604/368 |
| 5,267,992 | 12/1993 | Van Tilburg | 604/387 |
| 5,275,591 | 1/1994 | Mavinkurve | 604/387 |
| 5,281,208 | 1/1994 | Thompson et al. | 604/378 |
| 5,324,278 | 6/1994 | Visscher et al. | 604/385.1 |
| 5,366,453 | 11/1994 | Zehner et al. | 604/386 |
| 5,382,245 | 1/1995 | Thompson et al. | 604/367 |

THIN, CURVED ABSORBENT ARTICLE HAVING ELASTICIZED EDGES

FIELD OF THE INVENTION

This invention relates to an absorbent article for absorbing body fluid and in particular menstrual fluid. More particularly, this invention relates to thin, flexible sanitary napkins having a tensioning device for imparting a curved configuration to the absorbent article.

BACKGROUND OF THE INVENTION

All manner and variety of absorbent devices or appliances have been configured for the absorption of body fluids, such as menses, and are well known. Sanitary napkins are the most frequently used of these devices.

In the formation of such absorbent devices for the absorption of human exudate, the sanitary napkin commonly includes a liquid-permeable bodyfacing cover, an absorbent, and a garment-facing liquid-impermeable baffle. These absorbent devices, whether utilized as diapers, incontinence garments or sanitary napkins are subject to failure resulting in the movement of fluid across the face of the cover and/or through the absorbent core and leaking onto the wearer or the wearer's undergarment. In the area of sanitary napkins, it has been suggested that at least 20–25 percent of all sanitary napkins have side leakage. This incidence of leakage increases especially for those sanitary napkins having increased absorbency designed primarily for medium to heavy flow.

To overcome the problem of side leakage, sanitary napkins have been constructed having elasticized sides that urge the sides upward or cause the sanitary napkin to form a cup shape.

Today's sociological changes have enabled women to become more active in sports and other types of physical activity. These changes have been complimented by a change in attire and have given women the option of wearing close body fitting clothing. Most sanitary napkins have a caliper of greater than 6 millimeters (mm) and can present a bulge adjacent to the pudendum when worn inside tight fitting shorts or pants. The overall size and configuration of the sanitary napkin can also restrict leg movement or cause discomfort when a woman participates in physical or sporting events. Recent developments in sanitary napkins have focused on ultrathin products which have less absorbent mass and, generally, have a caliper of less than about 5 mm.

In developing a thin sanitary napkin having a caliper of less than about 5 mm it has been observed that such products have a tendency to twist and bunch when worn. This is generally due to their highly flexible nature. Such twisting and bunching is detrimental to the efficacy of the product because the sanitary napkin is unable to absorb fluid that contacts its bodyfacing surface. Until now, the flexible nature of these ultrathin products has generally prevented the edges from being elasticized to form a concave surface or cup shape.

Therefore, there remains a need for a sanitary napkin that will be comfortable to wear while decreasing the chance of side leakage associated with the use of sanitary napkins during the menstrual period.

SUMMARY OF THE INVENTION

Briefly, this invention relates to disposable absorbent articles, and more particularly to sanitary napkins which are designed to absorb body fluids, such as menstrual fluid, and other excrements discharged by the body during a menstrual period. The absorbent article has traditional components, i.e., a fluid-pervious cover disposed toward the bodyfacing surface, a liquid-impermeable baffle disposed toward the garment-facing surface, and an absorbent positioned therebetween. The absorbent article includes a resilient member positioned between an outer periphery of the absorbent and the outer perimeter of the absorbent article. The resilient member extends along at least a portion of at least one longitudinal side of the absorbent article and preferably encircles the absorbent. The absorbent article has a concave shape directed toward the bodyfacing surface which is accomplished by attaching to the resilient member a tensioning device. When the tensioning device is relaxed it constrains the absorbent article to form a cup shape configuration with the central portion of the absorbent article forming the lowest surface. This configuration allows the central portion to act as a reservoir providing additional time for liquid to be absorbed into the absorbent. The presence of the tensioning device and the resilient member along the longitudinal side provides the absorbent article with a central receiving portion that is lower than the sides making side leakage virtually impossible.

It is the general object of this invention to provide an absorbent article having improved side leakage protection. A more specific object of this invention is to provide a sanitary napkin that has an arcuate configuration forming a concave shape directed toward the bodyfacing surface.

It is an additional object of this invention to provide a sanitary napkin which is thin and flexible and offers an enhanced fit, added comfort and a low degree of wearing awareness.

These and other objects, features and advantages are readily apparent when considered in reference to the following specification and the accompanying drawings. It is to be understood that the inventive concept is not to be considered limited to the construction disclosed except as determined by the scope of the appended claims.

DETAILED DESCRIPTION OF THE PREFERRED EMBODIMENTS

The present invention relates to an absorbent article having close body contact and improved side leakage protection. Although described hereafter as a sanitary napkin, it is to be understood that the invention can be adapted for use in disposable diapers, adult incontinence devices and the like.

Figure 1:
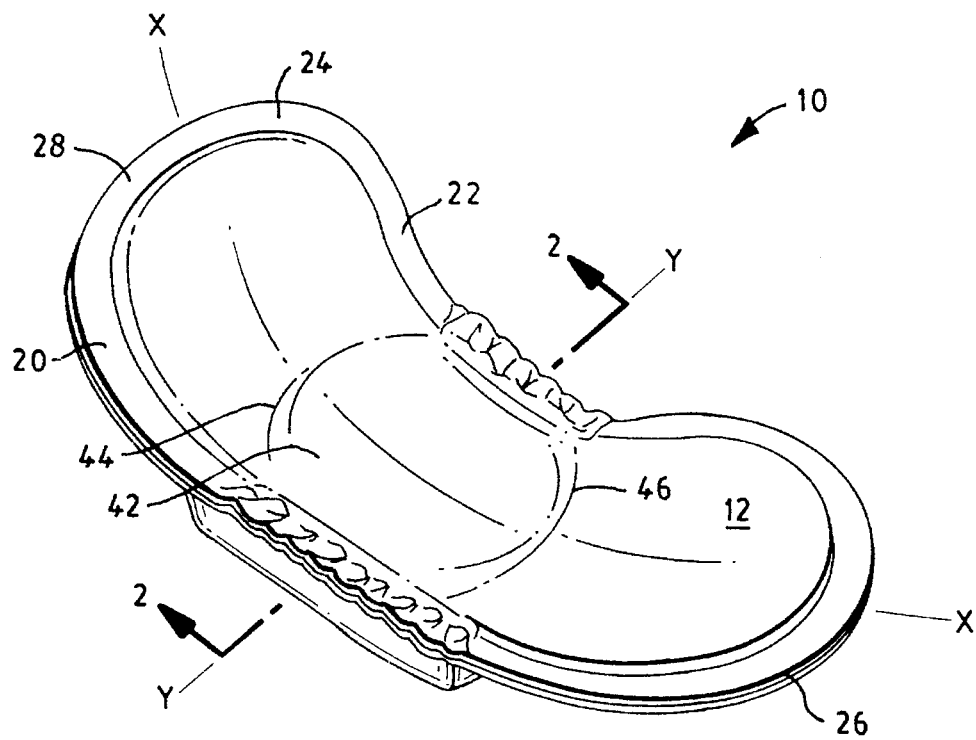
FIG. 1 is a perspective view of an absorbent article, illustrated as a sanitary napkin, generally showing a concave curvature toward the bodyfacing surface.
Figure 2:
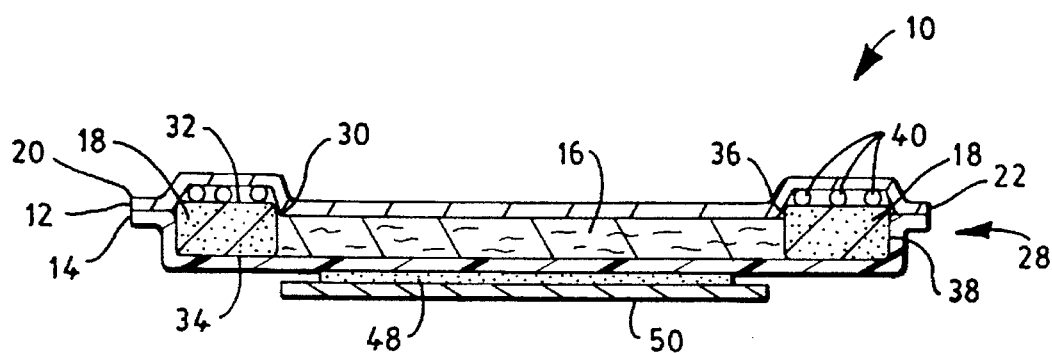
FIG. 2 is a transverse cross-sectional view of the absorbent article taken along line 2—2 of FIG. 1.

Referring to FIGS. 1 and 2, the sanitary napkin 10 includes a liquid-permeable, bodyfacing cover 12, a garment-facing, liquid-impermeable, baffle 14, an absorbent 16 intermediate the cover 12 and the baffle 14, and a resilient member 18 positioned adjacent to at least a portion of the outer periphery of the absorbent 16. The sanitary napkin 10 has a pair of spaced apart longitudinal edges 20 and 22 and ends 24 and 26. The longitudinal edges 20 and 22 in combination with the ends 24 and 26 collectively form the outer perimeter 28 of the sanitary napkin 10.

The sanitary napkin 10 can have a length ranging from about 150 mm to about 300 mm and a width ranging from about 50 mm to about 175 mm at its widest point. The term "length" as used herein means the longitudinal dimension measured along a longitudinal axis X—X from end 24 to end 26. The term "width" as used herein means the lateral dimension measured along a transverse axis Y—Y from one longitudinal edge 20 to the other longitudinal edge 22 across its widest portion.

Looking at some of the elements of the sanitary napkin 10 more specifically, the cover 12 is fluid-pervious and is adapted to reside on that side of the sanitary napkin 10 to be in contact with the body of the wearer. The cover 12 is provided for comfort and conformability and functions to direct fluid to the underlying absorbent 16. The cover 12 can be constructed of any woven or nonwoven material which is easily penetrated by body fluid contacting its surface. Preferably, the cover 12 is made of a material which allows the passage of fluid without wicking it appreciably in a horizontal plane parallel to the cover 12. Furthermore, the cover 12 should retain little or no fluid in its structure so that it provides a relatively dry surface next to the skin. Generally, the cover 12 is a sheet of material having a width sufficient to overlie the bodyfacing side of the absorbent 16.

The cover 12 can be constructed of bonded carded webs of polyester, polypropylene, polyethylene, nylon, or other heat-bondable fibers. Other polyolefins, such as copolymers of polypropylene and polyethylene, liner low-density polyethylene, finely perforated film webs and net material also work well. Other suitable materials are composite apertured materials of polymer and a nonwoven fabric material. The composite sheets are generally formed by extrusion of polymer onto a web of spunbond material to form an integral sheet. This material is preferred because the outer fabric surface is not irritating to the skin of the wearer and has a cushion feel.

Another material for the cover 12 is a spunbond web of polypropylene. The web can contain from about 1 to 6 percent titanium dioxide pigment to give it a clean white appearance. The most preferred polypropylene webs have a weight of between about 10 and 40 grams per square meter. Desirably, the weight is between about 25 and about 35 grams per square meter.

The liquid-permeable cover 12 can also contain a plurality of apertures (not shown) formed therein. Such apertures can be arranged along the longitudinal central axis X—X if desired or localized in a specifically desired region of the sanitary napkin 10. The apertures are intended to increase the rate at which body fluids can penetrate down into the first absorbent layer 12. With apertures present, body fluid, which is deposited at or near the apertures, rapidly migrates into the absorbent 16. This helps maintain a perceivably drier surface than when the apertures are not present. Therefore, while the apertures are not essential, a functional advantage is obtained by their use.

The liquid-permeable cover 12 can also be treated with a surfactant to make it more hydrophilic and, thereby, aid in the absorption of the liquid. The surfactant can include topical additions or internally applied materials like polysiloxanes.

The absorbent 16 can be made from one or more materials that are hydrophilic, compressible, conformable and nonirritating to the wearer's skin, and capable of absorbing and containing body exudates. Acceptable materials are well known in the art and include, for example, various natural or synthetic fibers, wood pulp fibers, regenerated cellulose or cotton fibers, or a blend of pulp and other fibers, meltblown polymer, such as polyester, and polypropylene. Meltblown polymers are taught in U.S. Pat. No. 4,798,603 issued to Meyer et al. and assigned to the present assignee. The entire disclosure of this patent is incorporated herein by reference. The absorbent 16 may also be comprised of a composite of absorbent materials used in absorbent articles, including multiple layers of cellulose wadding, rayon fibers, cellulose sponge, hydrophilic synthetic sponge, such as polyurethane, and the like.

The absorbent 16 generally has an outer periphery 30 located inward from the outer perimeter 28 of the sanitary napkin 10 so that the cover 12 and the baffle 14, in combination, will enclose the absorbent 16. The absorbent 16 can be manufactured in a wide variety of sizes and shapes, such as rectangular, hourglass, oval, etc. The total absorbent capacity of the absorbent 16 should be compatible with the design exudate loading in the intended use of the sanitary napkin 10. Preferably, the absorbent 16 is symmetrically configured for ease of manufacture. Another advantage is that no conscious effort is required by the wearer to properly place the sanitary napkin 10 in the direction it should be worn. The cover 12 and the baffle 14 can be attached to the absorbent 16 by any means well known in the art, such as by spray-gluing or ultrasonic bonding.

The absorbent 16 may further contain superabsorbents which are effective in retaining body fluids. Superabsorbents have the ability to absorb a large amount of fluid in relation to their own weight. Typical superabsorbents used in absorbent articles, such as sanitary napkins, can absorb anywhere from about 5 to about 60 times their weight in body fluids. However, the absorption mechanism of the superabsorbents is usually slower than the rate of fluid absorption by cellulose fluff material. The placement of the superabsorbent particles is not critical but have been found to be effective when placed in the central portion of the sanitary napkin 10 as this provides additional time for the superabsorbent particles to absorb the body fluid.

The baffle 14 may be constructed from any desired material that is liquid-impermeable on the garment-facing surface and preferably will permit the passage of air and moisture vapor out of the sanitary napkin 10 while blocking the passage of body fluids. A good material is a microembossed, polymeric film, such as polyethylene or polypropylene having a thickness of about 0.001 to about 0.005 of an inch (0.025 to 0.13 millimeters). Bi-component films can also be used as well as woven and nonwoven fabrics which have been treated to render them liquid-impermeable. Another suitable material is a closed cell polyolefin foam. For example, a closed cell polyethylene foam having a thickness ranging from about 0.5 millimeters to about 10 millimeters.

As indicated, the liquid-impermeable baffle 14 is coextensive with the liquid-permeable cover 12. The baffle 14 can be adhered to the cover 12 in those areas where the cover 12 and the baffle 14 are in face-to-face contact. The method of adhering the cover 12 to the baffle 14, and optionally to the absorbent 16 as well, may be any method that does not leave a hard, uncomfortable residue that would be annoying to the wearer. Methods for joining the various materials are well known to those skilled in the art and include the use of hot melt adhesives in a uniform and continuous or non-continuous layer, patterned adhesives, pressure sensitive adhesives, double-sided tape, ultrasonic bonding, and heat sealing to name a few.

The resilient member 18 is positioned between the outer periphery 30 of the absorbent 16 and the outer perimeter 28 of the sanitary napkin 10 and preferably, is positioned immediately adjacent to the outer periphery 30 and along at least one of the longitudinal edges 20 or 22. The resilient member has four spaced apart surfaces: an upper surface 32 disposed toward the cover 12, a lower surface 34 disposed toward the baffle, an inner surface 36 disposed toward the absorbent 16 and an outer surface 38 disposed toward the perimeter 28 of the sanitary napkin 10. Preferably the resilient member 18 is positioned along both longitudinal edges 20 and 22. The resilient member 18 can have a length ranging from about 35 mm to extending the length of the sanitary napkin 10. Desirably, the resilient member 18 is symmetrically arranged about the transverse central axis Y—Y of the sanitary napkin 10. Preferably, the resilient member 18 encircles the absorbent 16.

The resilient member 18 can reside on top of the cover 12 or between the cover 12 and the baffle 14. Since the resilient member 18 will preferably be in contact with the body of the wearer, it is advantageous for the resilient member 18 to be covered by a material that is soft and compliant, such as the cover 12. It is therefore preferred that the resilient member 18 reside below the cover 12.

The resilient member 18 is desirably constructed of a flexible, resilient material and is preferably hydrophobic. The resilient member 18 can be constructed from hydrophobic polymer foams, such as, for example polyurethane foams. Other flexible, resilient materials may also be used in constructing the resilient member 18 such as those formed of foamed styrene butadiene, foamed polyethylene, foamed silicones, foamed vinyl plastics, soft sponge rubber, crosslinked and non-crosslinked closed cell foams and the like. Such foams can be obtained from Woodbridge Foam Fabricating, Inc., located at 1120 Judd Road, Chattanooga, Tenn., from the E.N. Murray Company, Inc., having offices in Denver, Colo. and Astro-Valcour, INC., having offices at 18 Peck Ave., Glens Falls, N.Y., and Youngbo America, Inc. located at 11816 Western Avenue, Stanton, Calif.

The resilient member 18 can also be hydrophilic or partially hydrophilic. A suitable hydrophilic material for use as a resilient member 18 is a compressed cellulosic sponge. The cellulosic sponge should have a pore size sufficient for absorbing the intended body fluid. For example, in the case where menses is intended to be absorbed the pores of the sponge would be larger than if a less viscous liquid, such as urine, was the intended substance to be absorbed.

It is important for wearer comfort that the resilient member 18 be stiff and resilient. The resilient member 18 should have a stiffness ranging from about 1000 to about 11,000 Gurley stiffness units, and preferably from about 1000 to about 10,000, and more preferably 1500 to about 9,000. Stiffness is determined in accordance with TAPPI method T543 pm-84 the disclosure of which is incorporated herein by reference and made a part hereof.

The resilient member 18 should have a width ranging from about 3 mm to about 12 mm and a height of about 0.5 mm to about to about 8 mm; preferably, the width is from about 1 mm to about 6 mm and the height is from about 6 mm to about 10 mm.

The sanitary napkin 10 also has a flexure-resistance of less than about 700 grams, preferably, less than about 400 grams, more preferably, less than about 300 grams and most preferably, less than 200 grams. The flexure-resistance is measured by the peak bending stiffness as determined by a test modeled after the ASTM D4032-82 CIRCULAR BEND PROCEDURE. This modified test is used for the purposes of the present invention and is, hereinafter, simply referred to as the "Circular Bend Procedure." The Circular Bend Procedure is a simultaneous multi-directional deformation of a material in which one face of a specimen becomes concave and the other face becomes convex. The Circular Bend Procedure gives a force value related to flexure-resistance, simultaneously averaging stiffness in all directions.

In the case of the present invention when carrying out the Circular Bend Procedure, separate samples of the sanitary napkins are taken along the longitudinal central axis X—X from the absorbent 16.

The apparatus necessary for the Circular Bend Procedure is a modified Circular Bend Stiffness Tester, having the following parts: A smooth-polished steel plate platform which is 102.0×102.0×6.35 millimeters having an 18.75 millimeter diameter orifice. The lap edge of the orifice should be at a 45 degree angle to a depth of 4.75 millimeters. A plunger having the following dimensions: overall length of 72.2 millimeters, a diameter of 6.25 millimeters, a ball nose having a radius of 2.97 millimeters and a needle-point extending 0.88 millimeters therefrom with a 0.33 millimeter base diameter and a point having a radius of less than 0.5 millimeters is used for the test. The plunger is mounted concentrically with the orifice having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force measurement gauge is also needed. An Instron inverted compression load cell having a load range of from about 0.0 to about 2000.0 grams works fine.

An actuator, and more specifically the Instron Model No. 1122 having an inverted compression load cell. The Instron 1122 is made by the Instron Engineering Corporation of Canton, Mass.

Since the present invention is concerned with the flexibility of the significant absorbent portions of the sanitary napkin 10, a number of different specimens should be tested from each sanitary napkin 10 containing the absorbent 16. Specimens having portions in which only the cover 12 and/or the baffle 14 are present should not be tested. Therefore, a number "Y" of different test specimens should be tested from each sanitary napkin 10. If any of the significant absorbent portions meet the parameters of this test, then the sanitary napkin 10 satisfies the test. The test specimens should not be folded, bent or compressed by the test person, and the handling of specimens must be kept to a minimum and to the edges to avoid affecting flexural-resistance properties.

In order to perform the procedure for this test, as explained below, five representative sanitary napkins are necessary. From one of the five napkins to be tested, some number "Y" of 37.5×37.5 millimeter test specimens are cut. From the four remaining sanitary napkins 10, an equal number "Y" of specimens, identical to the specimens cut from the first sanitary napkin 10, are cut. Thus, the test person should have "Y" number of sets with each set having five identical specimens.

The procedure for the Circular Bend Procedure is as follows. The specimens are conditioned by leaving them in a room which is 21±1° C. and 50±2% Relative Humidity for a period of at least two hours. The test plate is leveled. The plunger speed is set at 50.0 centimeters per minute per full stroke length. A specimen is centered on the orifice platform below the plunger such that the cover 12 of the specimen is facing the plunger and the baffle 14 of the specimen is facing the platform with the release paper removed from any adhesive on the garment surface of the specimen and the adhesive sprinkled with corn starch, talc or any other suitable composition to eliminate the adhesive tack. The indicator zero is checked and adjusted, if necessary. The plunger is actuated. Touching the specimen during the test should be avoided. The maximum force reading to the nearest gram is recorded. The above steps are repeated until all five of the identical specimens have been tested.

The peak bending stiffness for each specimen is the maximum force reading for that specimen. From the "Y" number of sets, each set of five identical specimens is tested. The five values received for that set are then averaged. Thus, the test person now has an average value for each of the "Y" identical sets of specimens tested. If any of the significant absorbent portions of the sanitary napkin have the requisite flexure-resistance, then the sanitary napkin 10 satisfies the parameters of this test. Therefore, the flexure-resistance for a particularly designed sanitary napkin 10 is the greatest of these average peak bending stiffnesses.

Because of the flexibility of the sanitary napkin 10, it is likely that the sanitary napkin 10 will be relatively thin. It is preferred to keep the sanitary napkin 10 thin so that it will be unobtrusive and the user will have a low awareness of the sanitary napkin 10 while it is being worn. Accordingly, the caliper of the sanitary napkin 10 is less than about 5 mm, preferably less than about 4 mm, and most preferably, is less than about 3 mm.

The caliper of the sanitary napkin 10 at any location can be measured in accordance with the following procedure. All measurements are made on newly unpacked absorbent products. Each napkin should be removed from its package for at least 30 minutes and handled carefully to avoid compressing, or otherwise affecting the properties thereof. Unless otherwise stated, all tests are performed at a Relative Humidity of 50%±2% and a temperature of 73° F. and with any peel strip removed and the adhesive blocked using talc or corn starch. It is preferred that at least one measurement be taken inward from the resilient member 18.

A comparator gauge, (Ames, Model 130 with a dial indicator Model 482, available from the B.C. Ames, Company of Waltham, Mass.) is needed. The comparator gauge should typically have a circular comparator foot made of aluminum and a weight of 10.0 grams and a contact surface of 5.16 square centimeters. The gauge is provided with an 80.0 gram stainless steel weight to provide a total of 0.25 psi pressure. If due to the shape of the region to be tested, it is not possible to use a circular comparator foot and achieve an accurate measurement of the region, a 1"×¼" rectangular comparator foot should be used and a test weight should be used that provides a total pressure of 0.25 psi. The comparator gauge is first zeroed. The weight is then placed on the spindle extending above the comparator dial. The comparator foot is then raised and the napkin is placed on the base plate, garment surface down. The napkin is positioned on the base plate so that when the foot is lowered it is in the region of the napkin for which the measurement is desired. The sanitary napkin 10 should have as few wrinkles as possible before testing. Gently lower the foot onto the napkin. Determine the napkin caliper by reading the comparator dial 30 seconds after the foot comes in contact with the napkin.

Referring to FIG. 2, the sanitary napkin 10 further includes a longitudinally oriented tensioning means 40. Suitable materials from which the tensioning means 40 can be constructed include rubber, stretch bonded laminates, polyurethanes, heat shrinkable materials, and preferably, elastomeric materials such as elastic strips and/or strands. For the purposes of comfort, it is desired that the elastomeric material have a width ranging from about 1.5 mm to about 8 mm in width, and preferably about 2 mm to about 4 mm. Elastic materials having a width much greater than about 8 mm tends to chafe and become uncomfortable for the wearer.

Another method of introducing elastic is by utilizing an extrudable elastic which can be initially extruded as a liquid and upon cooling becomes both an adhesive and an elastic. An example of such a product is described in U.S. Pat. No. 4,259,220 assigned to H.D. Fuller Co. in St. Paul, Minn. the disclosure of which is incorporated herein by reference and made a part hereof.

Figure 3:
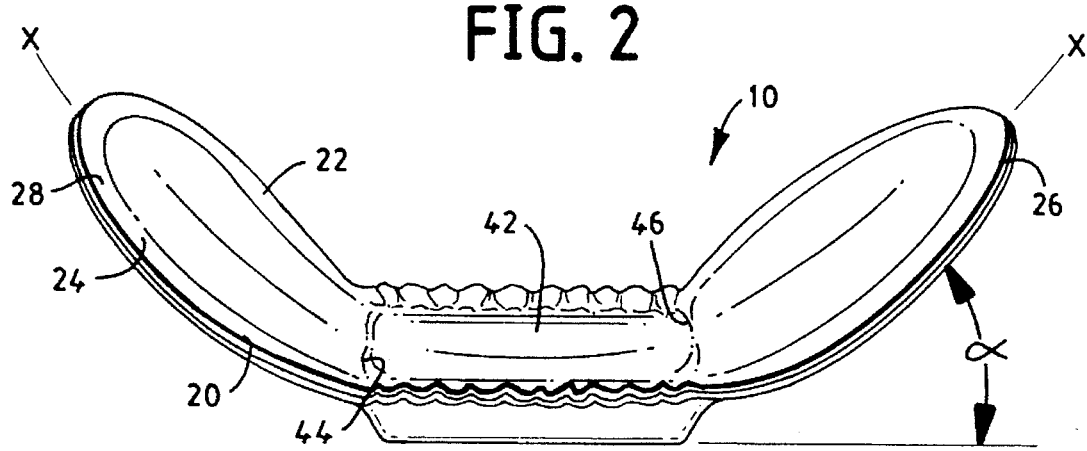
FIG. 3 is a side perspective view of the absorbent article illustrating the arcuate shape.

Referring to FIG. 3, the tensioning device 40 imparts to the sanitary napkin 10 a concave shape directed toward the cover 12. The general configuration of the sanitary napkin 10 can be seen by reference to FIG. 1. In the central region 42 there are fold lines 44 and 46. The extent of the folds 44 and 46 is dependent upon the width and length of the tensioning means 40, the stiffness of the absorbent 16 and resilient member 18, as well as the degree of elasticity of the elastomeric material. These factors are balanced, so that, the sanitary napkin 10 acquires the arcuate configuration. As used herein the term "arcuate" means that when one transverse end 24 of the sanitary napkin 10 is placed on a planar surface, the angle, alpha, formed by the outer profile along the longitudinal axis X—X of the sanitary napkin 10 to other transverse end 26 and with the plane upon which the sanitary napkin 10 rests is between 15 degrees and 90 degrees.

The tensioning means 40 can be secured to at least a portion of the resilient member 18, and preferably is superposed over a portion of the resilient member 18 and is secured to the upper surface 32. The tensioning device 40 can be secured to resilient member 18 by means well known in the art, such as, for example, using adhesives or a discontinuous ultrasonic bond.

Referring again to FIG. 2, the sanitary napkin 10 can be provided with attachment adhesive 48 applied to the garment-facing surface of the baffle 14. The adhesive 48 can be made from any known pressure-sensitive material. As used herein the term "pressure sensitive" refers to any releasable adhesive or releasable tenacious means. Adhesive compositions suitable for sanitary napkins, includes, for example, the water-based pressure-sensitive adhesives such as acrylate adhesives. Alternatively, the adhesive may comprise rapid setting thermoplastic "hot melt," rubber adhesives or two-sided adhesive tape. As is customary in the art, the adhesive 48 can be covered by a protective peel strip 50 such as a Kraft paper that is silicone coated.

In use, the wearer removes the peel strip 50 and attaches the sanitary napkin 10 to the inside surface of her undergarment. The adhesive strips 48 allow the sanitary napkin 10 to remain in position to receive discharged liquids.

While the particular embodiments of the present invention have been illustrated and described, it would be obvious to those skilled in the art that various other changes and modifications can be made without departing from the spirit and scope of this invention. It is therefore intended to cover in the appended claims all such changes and modifications that are within the spirit and scope of this invention.

We claim:

1. An absorbent article having a longitudinal side, an outer perimeter, a bodyfacing surface and a garment-facing surface, said absorbent article comprising:
   a) a liquid-permeable cover disposed proximate said bodyfacing surface;
   b) a liquid-impermeable baffle disposed proximate said garment-facing surface;
   c) an absorbent positioned intermediate said cover and said baffle, said absorbent having an outer periphery disposed inward from said outer perimeter;
   d) a resilient member encircling said absorbent and positioned immediately adjacent to said outer periphery; and
   e) tensioning means for imparting an arcuate configuration to said absorbent article, said tensioning means being secured to a portion of said resilient member, wherein said tensioning member produces at least one fold in said bodyfacing surface.

2. The absorbent article of claim 1 wherein said resilient member is a polyolefin foam.

3. The absorbent article of claim 1 wherein said resilient member is a compressed cellulosic sponge.

4. The absorbent article of claim 1 wherein said resilient member has a Gurley stiffness ranging from about 1000 to about 11,000.

5. The absorbent article of claim 4 wherein said resilient member has a Gurley stiffness of from about 1500 to about 9,000.

6. The absorbent article of claim 1 wherein said resilient member has a width ranging from about 3 millimeters to about 12 millimeters and a height of about 0.5 millimeters to about 8 millimeters.

7. The absorbent article of claim 6 wherein said resilient member has a width ranging from about 1 millimeters to about 6 millimeters.

8. The absorbent article of claim 1 wherein said tensioning means is an elastomeric material.

9. The absorbent article of claim 8 wherein said elastomeric material is an elastic strip having a width ranging from about 1.5 millimeters to about 8 millimeters.

10. The absorbent article of claim 9 wherein said elastic strip is superposed over a portion of said resilient member.

11. The absorbent article of claim 1 having a flexure-resistance of less than about 700 grams.

12. The absorbent article of claim 1 having a flexure-resistance of less than about 400 grams.

13. The absorbent article of claim 1 having a caliper of less than about 5 millimeters.

14. An absorbent article having a longitudinal side, an outer perimeter, a bodyfacing surface and a garment-facing surface, said absorbent article comprising:
   a) a liquid-permeable cover disposed proximate said bodyfacing surface;
   b) a liquid-impermeable baffle disposed proximate said garment-facing surface;
   c) an absorbent positioned intermediate said cover and said baffle, said absorbent having an outer periphery disposed inward from said outer perimeter;
   d) a resilient member encircling said absorbent and positioned between said outer perimeter and said outer periphery; and
   e) tensioning means for imparting an arcuate configuration to said absorbent article, said tensioning means being secured to a portion of said resilient member, and said absorbent article having a flexure-resistance of less than about 700 grams and a caliper of less than about 5 millimeters.

15. The absorbent article of claim 14 wherein said resilient member is a polyolefin foam having a resiliency of from about 15 percent to about 60 percent.

16. The absorbent article of claim 15 wherein said polyolefin foam has a width ranging from about 3 millimeters to about 8 millimeters.

17. The absorbent article of claim 14 wherein said tensioning means is an elastic strip having a width ranging from about 1.5 millimeters to about 8 millimeters.

18. A sanitary napkin having a longitudinal side, an outer perimeter, a bodyfacing surface and a garment-facing surface, said sanitary napkin comprising:
   a) a liquid-permeable cover disposed proximate said bodyfacing surface;
   b) a liquid-impermeable baffle disposed proximate said garment-facing surface;
   c) an absorbent positioned intermediate said cover and said baffle, said absorbent having an outer periphery disposed inward from said outer perimeter;
   d) a polyolefin foam resilient member encircling said absorbent; and
   e) tensioning means for imparting an arcuate configuration to said sanitary napkin, said tensioning means including an elastic strip secured to said resilient member, said absorbent article having a flexure-resistance of less than about 300 grams and a caliper of less than about 5 millimeters, wherein said tensioning member produces at least one fold in said bodyfacing surface.

* * * * *